(12) United States Patent
Levin

(10) Patent No.: US 9,320,733 B2
(45) Date of Patent: Apr. 26, 2016

(54) ASSESSMENT AND MODULATION OF CEREBROSPINAL FLUID FOR HEAD PAIN

(76) Inventor: Bruce H. Levin, Philadelphia, PA (US)

( * ) Notice: Subject to any disclaimer, the term of this patent is extended or adjusted under 35 U.S.C. 154(b) by 671 days.

(21) Appl. No.: 13/225,667

(22) Filed: Sep. 6, 2011

(65) Prior Publication Data

US 2012/0172751 A1    Jul. 5, 2012

Related U.S. Application Data

(60) Provisional application No. 61/380,020, filed on Sep. 3, 2010.

(51) Int. Cl.
| | |
|---|---|
| *A61K 38/43* | (2006.01) |
| *A61K 31/433* | (2006.01) |
| *A61K 31/00* | (2006.01) |
| *A61K 31/196* | (2006.01) |
| *A61K 31/341* | (2006.01) |
| *A61K 31/382* | (2006.01) |
| *A61K 31/7048* | (2006.01) |
| *A61B 5/03* | (2006.01) |

(52) U.S. Cl.
CPC .............. *A61K 31/433* (2013.01); *A61K 31/00* (2013.01); *A61K 31/196* (2013.01); *A61K 31/341* (2013.01); *A61K 31/382* (2013.01); *A61K 31/7048* (2013.01); *A61B 5/031* (2013.01); *A61B 5/032* (2013.01)

(58) Field of Classification Search
CPC ....................................................... A61K 38/43
See application file for complete search history.

(56) References Cited

U.S. PATENT DOCUMENTS 7,513,883 B2 * 4/2009 Glenn ............................... 604/8

OTHER PUBLICATIONS

Bret et al. (Is normal pressure hydrocephalus a valid concept in 2002? A reappraisal in five questions and proposal for a new designation of the syndrome as "chronic hydrocephalus". J Neurol Neurosurg Psychiatry 2002;73:9-12).*
The Mayfield Clinic and Spine Institute (Lumbar Puncture (Spinal Tap) basic level. 2002 pp. 1-2).*
Jeon et al. (Acetazolmaide-responsive Hereditary Paroxysmal Ataxia. J. Korean Med. Sci. 1998 13:196-200).*
Battsini et al. (A new CACNA1A gene mutation in acetazolamide-responsive familial hemiplegic migraine and ataxia. Neurology (1999) 53(1): pp. 1-9).*

* cited by examiner

*Primary Examiner* — Karen Cochrane Carlson
*Assistant Examiner* — Natalie Moss
(74) *Attorney, Agent, or Firm* — Michael B. Fein; Eckert Seamans Cherin & Mellott, LLC

(57) ABSTRACT

The disclosure relates to the discovery that certain cerebrovascular disorders in humans who exhibit seemingly normal intracranial pressure (ICP) and do not exhibit hydrocephalus can be alleviated or prevented by reducing ICP in the human. Disorders of this type are herein designated normotensive, nonhydrocephalus tenso-responsive cerebrovascular disorder (NNTCDs). The disclosure describes methods of relieving head pain and other symptoms of NNTCDs, for example by withdrawing cerebrospinal fluid (CSF) from the subarachnoid space of a human or by administering a pharmaceutical agent that modulates CSF production, uptake, or both. Methods of assessing whether a human is afflicted with one or more NNTCDs are also described. The disclosure describes numerous pharmaceutical compositions suitable for administration to humans afflicted with NNTCDs to alleviate or prevent such disorders. Such compositions can, for example, include both a CSF-reducing agent and a symptomatic (e.g., head pain) relief agent.

1 Claim, No Drawings

ASSESSMENT AND MODULATION OF CEREBROSPINAL FLUID FOR HEAD PAIN

CROSS-REFERENCES TO RELATED APPLICATIONS

This application is entitled to priority pursuant to 35 U.S.C, §119(e) to U.S. provisional patent application 61/380,020, which was filed on 3 Sep. 2010.

BACKGROUND OF THE DISCLOSURE

The disclosure relates generally to the field of alleviating headaches and other head pain.

The human central nervous system (CNS; i.e., the brain and spinal cord) are surrounded by three membranous structures, the distal structure designated the dura mater, the proximal structure designated the pia mater, and the arachnoid (or "arachnoid mater") being interposed between these two. The subarachnoid space (i.e., the cavity between the arachnoid and the enclosed CNS components) is filled with a liquid designated cerebrospinal fluid (CSF). CSF also fills the ventricles of the brain and the central canal of the spinal cord.

CSF is a liquid that is normally clear in healthy individuals. In addition to supporting and cushioning the CNS from physical trauma, CSF can serve as a medium for transport of nutrients, metabolites, or other compounds across the blood-brain barrier.

There is a natural flow of CSF that is attributable to production of CSF (primarily by choroid plexus tissues, with lesser production at cerebral vascular and ventricular surfaces), migration therefrom through brain ventricles, across brain and spinal cord surfaces through the subarachnoid space, and reabsorption into the bloodstream through arachnoid granulations and lymphatic channels. Although the rate of CSF formation appears to vary among individuals, production rates on the order of 500 milliliters per day are not unusual. The volume of CSF-filled space within the CNS of a normal, healthy individual is on the order of about 135-150 milliliters, indicating that the normal daily turnover of CSF in the CNS of a normal, healthy individual is roughly 3-4 times per day.

CSF can be accessed by a variety of known techniques, among the most common of which is lumbar puncture (LP). In LP procedures, the tip of a needle is inserted into the subarachnoid space in the spinal column, typically between the L3 and L4 vertebrae or between the L4 and L5 vertebrae (i.e., to avoid contact between the needle and the spinal cord, which typically does not extend to these positions). The subarachnoid space can thus be accessed by way of the lumen of the needle, CSF can be withdrawn through the lumen, or liquid can be introduced into the subarachnoid space to mix with or displace CSF.

The subarachnoid space usually exists in a hyperpressurized state, relative to the extracorporeal atmosphere, meaning that if a channel is opened between the subarachnoid space and the outside of the body (e.g., via a LP needle having no flow regulator), CSF will initially flow from the subarachnoid space to the exterior of the body until the pressure within the subarachnoid space substantially equals the extracorporeal pressure. The pressure difference between the subarachnoid space and the extracorporeal atmosphere (the "intracranial pressure;" ICP) is typically on the order of about 20 centimeters of water (cmW; i.e., about 15 millimeter of mercury, mmHg) or less in a normal, non-diseased prone human at rest. Methods of assessing ICP are well known and include, for example, discrete manometric measurements made by way of LP and use of implanted ICP sensors.

In the past, others have recognized that abnormally high ICP (i.e., >25 cmW) can lead to or cause head pain and, if the abnormally high ICP is of sufficient duration and severity, it can result in serious or fatal brain damage. Common causes of abnormally high ICP include head trauma (especially that inducing cerebral edema or formation of intracranial heniatoma), intracranial tumor occurrence, infections such as meningitides, and hydrocephalus. Owing to the importance of relieving abnormally high ICP when it occurs, a variety of agents and techniques have been developed for reducing ICP.

A simple method of reducing ICP is simply draining CSF from the subarachnoid space, such as by way of a LP needle or a catheter (an "extraventricular drain") extending into a brain ventricle. Another physical methods of reducing localized ICP is installation of a shunt within the subarachnoid space (e.g., in instances in which CSF produced within a particular cerebral ventricle is constrained by abnormal CNS anatomical structure from normal flow through the subarachnoid space). Numerous devices suitable for draining CSF from the subarachnoid space are known, including devices generally designated "cerebral shunts" (e.g. ventriculoperitoneal shunts) and devices (e.g., lumboperitoneal shunts) intended for draining CSF from portions of the spinal column. Other fenestration methods for facilitating drainage of fluid from a tissue-delineated compartment are known, such as the AQUAFLOW brand collagen glaucoma drainage device (STAAR Surgical, Monrovia, Calif.), which has the ability to facilitate flow of intraocular fluid from beneath the cornea to the exterior of the eye (i.e., thereby relieving and preventing abnormally high intraocular pressure). Other known methods involve fenestration of the dura mater, such as optic nerve sheath decompression surgical techniques.

Numerous pharmaceutical agents are known to decrease the rate of CSF production, and use of such agents to reduce abnormally high ICP is known. Examples of such agents include acetazolamide (e.g., acetazolamide sold under the registered trademark DIAMOX, which trademark is owned by American Cyanamid Company, New York, N.Y.), topiramate (e.g., topiramate sold under the registered trademark TOPAMAX, which trademark is owned by Johnson & Johnson, New Brunswick, N.J.) and other known inhibitors of carbonic anhydrase, including methazolamide, dorzolamide (TRUSOPT, a registered trademark of Merck & Co., Inc., Whitehouse Station, N.J.). Furthermore, other agents are known to reduce the volume of CSF in human patients, including diuretics (e.g., bumetanide and furosemide).

Normal pressure hydrocephalus (normotensive hydrocephalus) is a condition in which ICP is not abnormally high (normotensive hydrocephalus patients often exhibit ICP of 15-20 cmW). Normotensive hydrocephalus patients usually exhibit urinary incontinence, gait anamolies, and dementia, but do not exhibit the classic hydrocephalus symptoms of headache, nausea, and vomiting. Brain ventricles are typically abnormally enlarged in normotensive hydrocephalus.

Head pain is a common occurrence and is symptomatic of a wide variety of physiological states, including many human diseases and disorders. Head pain can be attributable, for example, to trauma to the head or other body parts, migraine and other cerebroneurovascular disorders, stress and muscle tension, infections, sensitivity to chemicals, and many other causes. One particular type of headache is known to be associated with disruption of CSF homeostasis—so-called post dural puncture headache (PDPH). PDPH is attributable to loss of CSF through a puncture of the dura matter, such as occurs in the LP procedure. In PDPH, loss of CSF through the dural puncture site is believed to reduce the brain-protecting capacity of durally-retained CSF, leading to CNS-irritating traction between CNS components and their associated meninges which is experienced by the patient as head pain. PDPH can be treated by methods involving sealing of the puncture site, which results in increased volume and pressure of CSF.

It is common that the etiology of head pain (especially chronic head pain) cannot be determined from simple reports and examination of human patients. As a result, numerous treatment modalities are sometimes attempted, in the hope that one modality provides relief. Furthermore, there are patients for whom no previously known treatment modalities provide relief from their chronic head pain.

A need exists for additional methods of assessing and treating head pain, especially chronic head pain of previously inexplicable etiology. The present disclosure relates to such methods.

DETAILED DESCRIPTION

The disclosure relates to methods of assessing, alleviating, and preventing chronic head pain and other symptoms associated with excess CSF volume and/or pressure in humans who do not exhibit abnormally high ICP or hydrocephalus.

Definitions

As used herein, each of the following terms has the meaning associated with it in this section.

"LP" means lumbar puncture, as commonly understood in the fields of medicine and anesthesiology.

"CSF" means cerebrospinal fluid.

"ICP" means intracranial pressure (i.e., the pressure difference between subarachnoid CSF in a prone, resting human accessed by LP and the atmosphere surrounding the human's body). ICP can be assessed, for example, using a standard water-column manometer.

"Normal ICP" means ICP not greater than about 20 centimeters of water (cmW).

"Abnormally high ICP" means ICP greater than 25 cmW.

"CNS" means the central nervous system of a human, including the brain and spinal cord.

A "normotensive, nonhydrocephalus tenso-responsive cerebrovascular disorder" (NNTCD) is a human disorder characterized by exhibition in a prone, resting human of at least one symptom that is attributable to the effect of ICP on a neural or vascular structure of the CNS of the human, despite the fact that the human exhibits neither abnormally high ICP nor abnormal accumulation of CSF in the brain.

A "normotensive CST-dependent headache" is a type of NNTCD characterized by head pain that is relieved by removal of CSF from the patient.

In the context of an NNTCD, a "symptomatic relief agent" is a pharmacological agent for which alleviation, inhibition, or prevention of a symptom of the NNTCD (e.g., head pain or tinnitus) is a known pharmacological effect of administering the agent to a human.

A "head pain relief agent" is a pharmacological agent for which alleviation, inhibition, or prevention of head pain is a known pharmacological effect of administering the agent to a human. A wide variety of head pain relief agents are known, including analgesics (e.g., aspirin, acetaminophen, narcotic analgesics, analgesic steroids, and non-steroidal anti-inflammatory drugs), triptans (e.g., sumatriptan, rizatriptan, and zolmitriptan), and gamma-aminobutyric acid analogs (e.g., gabapentin and pregabalin).

A "CSF-reducing agent" is a pharmacological agent which, when administered to a human, reduces the volume, the pressure, or both the volume and the pressure of CSF in the human.

A "CSF-reducing intervention" is a medical or surgical technique, or maneuver that causes reduction in the volume, the pressure, or both the volume and the pressure of CSF in a human upon Whom the technique or maneuver is performed. Examples of CST-reducing interventions include withdrawal of CST by LP, fenestration of a portion of the dura mater of the CNS, implantation of a shunt that facilitates flow of CSF from the subarachnoid space, and activation of a device that activatably facilitates flow of CSF from the subarachnoid space.

"Dorsonasal administration" of a composition and grammatical forms thereof mean delivery of the composition to the tissue lining the superior and/or dorsal surfaces of the nasal cavity in the vicinity of one or more nerve structures located near beneath such epithelial surface, including the sphenopalatine ganglion (SPG) and the olfactory bulb, for instance. Dorsonasal administration may be accomplished, for example, by topical administration of the composition to the region of the nasal epithelium overlying the SPG or to the surface of the nasal epithelium near the region of the nasal epithelium overlying the SPG. Such administration may also be accomplished, for example, by injecting the composition directly into the SPG or by injecting the composition into or otherwise administering the composition to a tissue or fluid near the SPG, whereby a component of the composition is capable of diffusing through any tissue or fluid which may be interposed between the site of injection or administration and the SPG.

DETAILED DESCRIPTION

The disclosure relates to methods of alleviating one or more symptoms of a normotensive, nonhydrocephalus tensoresponsive cerebrovascular disorder (NNTCD) in a human afflicted with such a disorder. In these methods, intracranial pressure (ICP) is reduced in the human by an amount and for a period sufficient to relieve the symptom. NNTCDs were previously not recognized as a distinct type of disorder. Furthermore, involvement of ICP in NNTCDs (or symptoms associated with NNTCDs) was previously not appreciated. It is believed that, for at least these reasons, others have not previously attempted to prevent alleviate NNTCDs or their symptoms using methods known to reduce ICP.

In view of the disclosure herein that NNTCDs can be prevented or alleviated by decreasing or relieving ICP, a wide variety of previously-known techniques and agents can be used to relieve patients afflicted with these disorders or at risk of developing them. Furthermore, disclosure herein of the involvement of ICP in the etiology and symptomology of such disorders facilitates diagnosis of the existence and severity of these disorders in humans.

Some humans do not exhibit abnormally high ICP (i.e., their CSF is "normotensive") or hydrocephalus (i.e., their brain ventricles do not appear to be abnormally large and they have no apparent abnormal accumulation of CSF), but nonetheless exhibit symptoms of cerebrovascular disorders. Symptoms of these disorders include head, face, neck, and/or shoulder pain, tinnitus, numbness of the extremities, generalized weakness, loss of smell, visual field changes, dyscoordination, motor disorders, psychological disorders, lack of concentration, attention deficits, attention deficit and hyperactivity disorders, chronic daily headaches, tension headaches, cluster headaches, and cranial nerve dysfunctions. In such patients, papilledema normally associated with intracranial hypertension is not present. The present disclosure is believed to demonstrate for the first time that these nonnontensive, non-hydrocephalus cerebrovascular disorders are responsive to reduction of ICP, and they are therefore designated "tenso-responsive." This combination of characteristics is what leads to the designation herein of such disorders as normotensive, nonhydrocephalus tenso-responsive cerebrovascular disorders (NNTCDs).

Without being bound by any particular theory of operation, it is believed that the likelihood that an individual will exhibit pathological symptoms (e.g., head pain or dizziness) attributable to the effect of ICP on intracranial or other CNS nerve and blood vessel function varies more significantly among individuals than was previously appreciated. The present discloser has recognized that at least some individual humans exhibit greater susceptibility to ICP-associated pathology and symptomology than others. For humans having greater-than-average susceptibility, ICP that is not generally considered abnormally high (at least on a population-wide basis) can adversely impact normal functioning of nerves or blood vessels that are located in or adjacent to the subarachnoid space or are impinged by a tissue in or adjacent that space. By lowering ICP below a level that generates such adverse impact, symptoms of NNTCDs can be alleviated, eliminated, or prevented.

One type of NNTCD that can be treated using the compositions and methods described herein is a normotensive CSF-dependent headache. Such a headache is characterized by head pain experienced by a human patient who does not exhibit abnormally high ICP and who does not exhibit symptoms of hydrocephalus. Often there is no evident cause for the head pain, although it can be less severe when the patient is lying in a prone, supine, or lateral position and the severity can increase upon suddenly standing or sitting upright. A more definitive diagnosis of normotensive CSF-dependent headache can be made upon analysis of CSF. CSF pressure (i.e., essentially equivalent to ICP in a prone patient) is not abnormally high (i.e., not greater than 20 cmW), and withdrawal of a small amount (e.g., 1-25 milliliters via lumbar puncture) of CSF yields relief of head pain. Reintroduction of approximately the same amount of CSF (or other liquid) into the subarachnoid space of the patient will ordinarily result in resumption of head pain at about the same intensity.

In patients with normotensive CSF-deperident headache or other NNTCD, withdrawal of CSF (e.g., 1-50 milliliters, preferably withdrawn 1-5 milliliters at a time) from the subarachnoid space of the patient yields relief of head pain or other NNTCD symptoms.

Rather than physically withdrawing CSF, ICE can be reduced by administering a CSF-reducing agent to a human. Of course, physical withdrawal of CSF can be performed before, after, or simultaneously with administration of CSE-reducing agent. The amount of agent administered will depend on the characteristics and severity of the NNTCD, whether acute (i.e., nearly immediate to several hours) or chronic (from at least a few hours to one day or more) ICP reduction is desired, and other factors within the skill of an artisan in this field. The amount of CSF-reducing agent administered should be sufficient to at least acutely reduce ICP. Extended or timed-release formulations of CSF-reducing agents can be used, as can substantially any other known pharmaceutical form. The agents described herein can be administered orally, intravenously, intrathecally, intranasally (or dorsonasally), or by other routes.

In one embodiment, the CSF-reducing agent is a pharmaceutical agent, such as a carbonic anhydrase inhibitor, a diuretic, another CSF reducing agent, or a combination of these. Examples of suitable CSF-reducing agents include acetazolamide, topiramate, methazolamide, dorzolamide, bumetanide, and furosemide.

In addition to a CSF-reducing agent, a symptomatic relief agent can also be administered to the human in order to relieve one or more symptoms (e.g., head pain) of the NNTCD. The symptomatic relief agent can be administered before, after, or simultaneously with the CSF-reducing agent. By way of example, the symptomatic relief agent can be a head pain relief agent. The identity of the symptomatic relief agent is not critical, and depends on the nature of the symptom to be relieved, By way of example, the symptomatic relief agent can be a head pain relief agent selected from the group consisting of tricyclic antidepressants, non-steroidal anti-inflammatory drugs (NSAIDs), analgesic salicylates, triptans, narcotic analgesics, analgesic steroids, acetaminophen, and gamma-aminobutyric acid analogs. Examples of suitable head pain relief agents include amytriptyline, ibuprofen, naproxen, fenoprofen, ketoprofen, flurbiprofen, oxaprozin, indomethacin, sulindac, etodolac, ketorolac, diclofenac, nabumetorie, piroxicam, meloxicam, terioxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, gabapentin, pregabalin, sumatriptan, rizatriptan, and zoinntriptan.

Instead of administering a CSF-reducing agent to the human, IGP can be reduced by installing a CSF shunt that drains the subarachnoid space. The shunt can drain CSF from the subarachnoid space into a body cavity such as the peritoneal space, the interior of the gut, or the extraocular space of the eye socket. Alternatively, the shunt can drain CSF from the subarachnoid space to an extracorporeal location. The shunt can drain CSF from a brain ventricle, or from a subdural space along the spine, for example.

Also disclosed herein is a method of assessing whether a human is afflicted with an NNTCD. The method includes acutely altering ICP in the human and assessing severity of a symptom of the NNTCD before and after altering the ICP. Greater severity of the symptom at higher ICP is an indication that the human is afflicted with the NNTCD. ICP can be altered in the human by accessing the subarachnoid space of the human by way of a lumbar puncture and adding or withdrawing fluid (1 to 25 milliliters) from the subarachnoid space, for example.

Disclosed herein is a composition for alleviating head pain (or another symptom of an NNTCD) in a human afflicted with an NNTCD. The composition includes both a CSF-reducing agent and a head pain relief agent. The CSF-reducing agent is included in an amount sufficient to reduce at least one of the volume and the pressure of CSF in a human to whom the composition is administered. The head pain relief agent can be included in an amount sufficient to acutely reduce the head pain.

The disclosure also includes a drug regimen for sustained alleviation of a symptom of an NNTCD in a human afflicted with an NNTCD. The regimen includes
   A) an acute composition comprising
     i) a CSF-reducing agent in an amount sufficient to acutely reduce at least one of the volume and the pressure of CSF in a human to whom the composition is administered, and
     ii) a symptomatic relief agent in an amount to acutely reduce the symptom; and
   B) a chronic composition comprising the CSF-reducing agent in an amount sufficient to chronically reduce at least one of the volume and the pressure of CSF in a human to whom the composition is administered.

Theories of Operation and Conclusions Derivable

The following theories and conclusions reflect information deducible from observations described herein and from additional observations made by the inventor. The inventor recognizes that the efficacy of the methods and compositions described herein is not dependent on the accuracy or general applicability of the theories presented in this section.

Efficacy of the treatment modalities described herein may reflect regional differences in CSF pressures in the cranium and related structures versus the lumbar spine. The brain or other parts of the CNS may have regional or global compliance changes even at what have previously been recognized or characterized as normal ICP values. This may result in impaired flow of arterialized blood to structures, venous blood flow away from structures, and changes in neuronal function. Hence, compromised blood flow secondary to vascular disease, cardiac disease, vasoconstriction or shock may be further compromised secondary to these brain compliance changes with changing ICP. In individuals abnormally sensitive to ICP changes (or to ICP values normally considered at the high end of "normal"), these effects may be experienced as head pain, Compositions and methods disclosed herein for altering CSF pressure or volume (or for altering CSF tissue turgor) can effectively improve blood flow to areas of the brain adversely affected by individualized sensitivity to putatively "normal" ICP. This will decrease the damage from stroke, transient ischemic attacks, and other conditions and may decrease the gliosis and T2 signal changes common in headache and migraine patients, resulting in decreased loss of brain tissue.

Shunt Use

A shunt placed in the supraspinal areas may decrease the progression of Arnold chiari symptoms and pathology by decreasing the pressure gradient between the supra spinal and spinal areas.

A shunt may be made that may be set to drain at lower pressures than are currently done (i.e., simply be redesigning the shunt to emit CSF al ICP values lower than currently-installed shunts). There can be variable pressure controls associated with the shunt, as known to those skilled in the art. The shunt can be patient actuated to decrease CSF in the central neuraxis at any location or all multiple locations, such that a patient, observer, physician or applied algorithm can initiate, increase, decrease, or reverse drainage in accordance with patient symptoms. The shunt cam have a temperature sensor and can be equipped to lower or increase CSF or CNS temperatures to decrease symptoms or to aid in brain preservation. There can be a reservoir for containing or storing CSF so that CSF volume can be augmented from the reservoir. There can be a reservoir for drugs to be administered or a port to facilitate dosing. Furthermore, there can be a type of stimulator in or in proximity with the device. There can be oxygenated or nutritional substrates or free radical scavengers that can be delivered with the device or through the device to decrease symptoms or to aid in brain preservation.

It is also recognized that overproduction of CSF can be decreased by treating any underlying condition which causes this. Surgical, gamma knife, needle, heat, cold, chemical, drug, toxin, or other modalities may be used to damage or destroy cells or tissues producing or directing CSF flow to the CNS in order to decrease CSF production. CSF composition or content can also be altered should one or more components increase symptoms.

One or more dural or arachnoid tears, rents, windows, holes, incisions or the like can be made or placed at one or more :locations or on or more levels to facilitate CSF egress from the subarachnoid space at a rate or amount sufficient to decrease symptoms for a longer period than a single dural puncture or spinal tap. These may be repeatedly made, with increasing defect size or altered geometry to find the optimal number, size and configuration. The geometry of a given puncture or window maybe varied, (i.e., "pencil point" hole, linear incision, triangular window, or quadrilateral window) to maximize effect, and the orientation along the long and/or short axes of the dural or arachnoid tissues varied to optimize effect. Essentially, a balance between production and egress can be optimized, and it is recognized that this can vary within a given patient over time as compensatory or other homeostatic changes occur.

EXAMPLES

The subject matter of this disclosure is now described with reference to the following Examples. These Examples are provided for the purpose of illustration only, and the disclosure is not limited to these Examples, but rather encompasses all variations which are evident as a result of the teaching provided herein.

Example 1

One individual had 10 years of headache, some components of which were moderately successfully treated with facet, epidural, and occipital injections. Nonetheless, a major headache component persisted and was refractory to treatment to a variety of medications including Topamax. MRI showed normal findings except for minimal sella changes, without papilledema on exam. IIH was suspected, but CSF pressures on prone LP were 13-14 cmW. Yet after 3 ml of CSF were removed for analysis, the patient was questioned and noted slight decrease in headache intensity, which had been 10/10 on the VAS previously. The patient noted a further decrease in headache intensity with further CSF removal. When the patient was asked to extend her upper back and head upwards to decrease intracranial pressure the headache decreased further. Therefore more CSF was drained 10 ml total. Her headache was now gone entirely. Patient was placed on Diamox, and developed postdurai puncture headache 3 days later, but with total absence of her usual headache. Brief discontinuation of Diamox resulted in loss of her PDPH, without her usual headache recurring. Patient is symptom free on low dose Diamox. it is interesting to note that the patient's other headache subtypes have not recurred. This suggests a possible 2bl hit pathology, similar to 2bl crush pathology of radicular, plexus or peripheral nerves. The patient's MRI was entirely normal several years ago. This suggests that many patients may suffer from headaches or other symptoms related to either partially or entirely from CSF physiology which is suboptimum for a given patient. Hence, medications or procedures which are currently or may be subsequently discovered to be used to treat intracranial hypertension can be used to treat headache or other CNS/PNS symptoms either singularly, in combination or used together with known headache/symptom therapies. For example triptans may be combined with Diamox or diuretics, triptans may be combined with NSAM or Lumbar puncture, shunts or intraocular drainage procedures may be use singularly or together.

Use of altered CSF production, drainage, flow characteristics or manipulation of venous/arterial blood flow, circulation or volume dynamics in patients with intracranial normo- or hyper-tensive states and headache or other CNS symptomatology.

It is known that idiopathic intracranial HTN (IIH) may result in a variety of symptoms including headache or head, face, neck, or shoulder pain, tinnitus, numbness of the extremities, generalized weakness, loss of smell, visual changes, dyscoordination, cranial and other nerve dysfunction as well as other numerous nonspecific signs and symptoms. The intracranial hypertension may be from an intracranial mass, or from high CSF or other pressures in the absence of any identifiable cause. Certain medications may cause primary intracranial HTN.

Three theories exist as to why the pressure might be raised in IIH: an excess of CSF production/decreased drainage, increased volume of blood or brain tissue, or obstruction of venous drainage from the brain. Intracranial hypertension is defined as CSF pressures greater than 25 cmW measured in a lateral decubitus or prone position. Sometimes patients may have periods of varied or even normal IGPs, but these periods often coincide with decreased symptom severity. Diagnosis is suggested by papilledema or optic disc atrophy which is nearly always present, or decreased ventricle size or empty sella sign which are often present and confirmed by CSF pressures greater than 25 cmW in lateral decubitus position. What is not recognized and is a surprising discovery is that patients with normal or even low CSF pressures without papilledma or visual field changes may have one or more of the same symptoms and respond to similar therapies used to treat intracranial hypertension.

The inventor postulates that flow dynamics may be responsible, such as regional areas of turbulent flow, regional pressure heterogenicities, or more simply that CNS pressure susceptibility varies more among individuals than has previously been recognized. This latter phenomenon may be similar in concept as is vascular HTN which varies on an individual basis.

Previously, continuous CSF pressure monitoring would be performed to diagnose intracranial hypertension if a point measurement was low or normal. However this is costly time consuming inconvenient and only useful if the patient has intracranial hypertension. Hence, this will not diagnose normotensive non hydrocephalus, although this may used to correlate symptoms with CSF pressures. Author suggests noting response to CSF withdrawal by active and passive means. Furthermore, one or more instances of reinjection of collected CSF or other suitable fluid can be done to increase CSF volume and noting the effect of withdrawal and reintroduction of fluid to the CSF on the patient symptoms may be helpful in diagnosing symptomatic normotensive nonhydrocephalus (NNH, a type of NNTCD) or Irritable Brain Syndrome (IBS). This may be done in aliquots or other increments, or in a single trial of withdrawal of CSF and/or augmentation of CSF volume. Furthermore, positional changes, such as trendelenberg, or valsalva or other maneuver to increase CSF volume, may be used to diagnose NNE in that these may increase symptoms.

Also disclosed is the use of one or more of these treatment modalities or medications in the treatment of manifestations of other CNS disorders including but not limited to tinnitus, seizure, motor dysfunction, incoordination, ataxia, Parkinson's disease, tremor, fatigue, visual disturbances, loss of peripheral vision, loss of visual acuity, decreased hearing, abnormal hearing, psychological disorders including but not limited to depression, bipolar, or schizophrenic disease, substance abuse or addiction, as well as focal or non-focal neurological disorder, cranial nerve disorder, ADD, ADHD, or other concentration disorders, intellectual impairment, sleepiness, narcolepsy or suboptimal performance in cognitive, motor or emotive tasks.

Also disclosed is Diamox or similar agents for chronic daily or other headache not associated with intracranial hypertension as a single agent or in combination with other headache medications.

It is further postulated that methods disclosed herein may also effect a decrease of nerve, joint, other tissue or inflammatory volume or pressure will decrease symptoms or physiology of radiculopathy, spondylosis, spinal stenosis, muscle, nerve or other tissue pathology. Further it is postulated that Diamox and related compounds may alter transmembrane potentials, ion/cation, protein or molecular transport mechanisms thereby reducing symptoms of these pathologies.

Useful compositions described herein include Diamox or a related compound alone; Diamox and one of Topamax, Lyrica, Neurontin, and Cymbalta; Diamox and one or more NSAIDs; Diamox and a triptan, chroman or other migraine treatment agent; Diamox and oxytocin; and Diamox and a steroid, TNF inhibitor, substance P inhibitor, or other anti-inflammatory agent.

The method includes administration of Diamox or effective compound before, during or following interventional pain treatments including facet, epidural, trigger point, paraspinal, myofascial, nerve, joint, or other injection of steroid, other anti-inflammatory agent, local anesthetic, Botox or other agent known in the art.

The disclosure of every patent, patent application, and publication cited herein is hereby incorporated herein by reference in its entirety.

While the subject matter has been disclosed herein with reference to specific embodiments, it is apparent that other embodiments and variations of this subject matter can be devised by others skilled in the art without departing from the true spirit and scope of the subject matter. The appended claims include all such embodiments and equivalent variations.

What is claimed is:

1. A method of alleviating a symptom of a normotensive, non-hydrocephalus tenso-responsive cerebrovascular disorder (NNTCD) selected from the group consisting of head, face, neck, and shoulder pain, tinnitus, numbness of the extremities, generalized weakness, loss of smell, visual field changes, dyscoordination, and cranial nerve dysfunctions in a human afflicted with the NNTCD, the method comprising one or more steps selected from the group consisting of withdrawing CSF via a lumbar puncture (LP) step and administering a pharmaceutical agent that is topiramate pharmaceutical agent is topiramate; and if the human is thereby determined to be tenso-responsive, reducing ICP by one or more of said steps until the symptom is alleviated.

* * * * *